(12) United States Patent
Ramdas et al.

(10) Patent No.: US 8,362,064 B2
(45) Date of Patent: Jan. 29, 2013

(54) SULFONAMIDE COMPOUNDS FOR THE TREATMENT OF RESPIRATORY DISORDERS

(75) Inventors: Vidya Ramdas, Kondapur (IN); Harry Finch, Essex (GB); Craig Fox, Essex (GB)

(73) Assignee: Pulmagen Theraputics (Inflammation) Limited, Burnham (GB)

( * ) Notice: Subject to any disclaimer, the term of this patent is extended or adjusted under 35 U.S.C. 154(b) by 0 days.

(21) Appl. No.: 13/142,697

(22) PCT Filed: Dec. 23, 2009

(86) PCT No.: PCT/GB2009/002951
§ 371 (c)(1),
(2), (4) Date: Oct. 25, 2011

(87) PCT Pub. No.: WO2010/076553
PCT Pub. Date: Jul. 8, 2010

(65) Prior Publication Data
US 2012/0041043 A1 Feb. 16, 2012

(30) Foreign Application Priority Data

Dec. 30, 2008 (IN) .......................... 3324/CHE/2008

(51) Int. Cl.
A61K 31/415 (2006.01)
C07D 231/18 (2006.01)
A61P 11/08 (2006.01)
(52) U.S. Cl. ..................................... 514/407; 548/370.1
(58) Field of Classification Search ........................ None
See application file for complete search history.

(56) References Cited

U.S. PATENT DOCUMENTS

| 2002/0055651 | A1 | 5/2002 | Moran et al. |
| 2004/0229904 | A1 | 11/2004 | Bunnage et al. |
| 2004/0242622 | A1 | 12/2004 | Mammen et al. |
| 2005/0133417 | A1 | 6/2005 | Bahn et al. |
| 2005/0159448 | A1 | 7/2005 | McKinnell et al. |
| 2005/0171147 | A1 | 8/2005 | Brown et al. |
| 2005/0182091 | A1 | 8/2005 | Brown et al. |
| 2005/0272769 | A1 | 12/2005 | Linsell |
| 2006/0019991 | A1 | 1/2006 | McKinnell et al. |
| 2006/0106075 | A1 | 5/2006 | Cuenoud et al. |
| 2006/0106213 | A1 | 5/2006 | Konetzki et al. |

FOREIGN PATENT DOCUMENTS

| DE | 10258695 | | 6/2004 |
| EP | 0505321 | A1 | 3/1992 |
| EP | 1440966 | A1 | 7/2004 |
| EP | 1460064 | A1 | 9/2004 |
| EP | 1477167 | A1 | 11/2004 |
| JP | 05025045 | A | 7/1991 |
| WO | 93/18007 | A1 | 9/1993 |
| WO | 99/38845 | | 8/1999 |
| WO | 99/38845 | A1 | 8/1999 |
| WO | 99/64035 | A1 | 12/1999 |
| WO | 00/32585 | A1 | 6/2000 |
| WO | 00/53601 | A1 | 9/2000 |
| WO | 00/62766 | A2 | 10/2000 |
| WO | 00/75114 | A1 | 12/2000 |
| WO | 01/42193 | A1 | 6/2001 |
| WO | 01/83462 | A1 | 11/2001 |
| WO | 02/00679 | A2 | 1/2002 |
| WO | 02/10143 | A1 | 2/2002 |
| WO | 02/12265 | A1 | 2/2002 |
| WO | 02/12266 | A1 | 2/2002 |
| WO | 02/13812 | A1 | 2/2002 |
| WO | 02/066422 | A1 | 8/2002 |
| WO | 02/070490 | A1 | 9/2002 |
| WO | 02/076933 | A1 | 10/2002 |
| WO | 02/088167 | A1 | 11/2002 |
| WO | 02/100879 | A1 | 12/2002 |
| WO | 03/024439 | A1 | 3/2003 |
| WO | 03/035668 | A2 | 5/2003 |
| WO | 03/042160 | A1 | 5/2003 |
| WO | 03/042164 | A1 | 5/2003 |
| WO | 03/042229 | A1 | 5/2003 |
| WO | 03/048181 | A1 | 6/2003 |
| WO | 03/062259 | A2 | 7/2003 |
| WO | 03/064445 | A1 | 8/2003 |
| WO | 03/072539 | A1 | 9/2003 |
| WO | 03/072592 | A1 | 9/2003 |
| WO | 03/091204 | A1 | 11/2003 |

(Continued)

OTHER PUBLICATIONS

Birrell et al., "PPAR-γ agonists as therapy for diseases involving airway neutrophilia," Eur. Respir. J., 24(1):18-23 (2004).
Campbell, "The clinical significance of PPAR gamma agonism," Curr. Mol. Med. 5(3):349-363 (2005).
Curkendall et al., "Cardiovascular Disease in Patients with Chronic Obstructive Pulmonary Disease," Saskatchewan Canada Cardiovascular Disease in COPD Patients, Ann. Epidemiol., 16:63-70 (2006).
Cuzzocrea et al., "Reduction in the Evolution Murine Type III Collagen-Induced Arthritis by Treatment With Rosiglitazone, a Ligand of the Peroxisome Proliferator-Activated Receptor γ," Arthritis Rheumatism, 48(12):3544-3556 (2003).
Cuzzocrea et al., "Rosiglitazone, a ligand of the peroxisome proliferator-actived receptor-γ, reduces acute inflammation," European Journal of Pharmacology, 483(1):79-93 (2004).

(Continued)

*Primary Examiner* — Kamal Saeed
(74) *Attorney, Agent, or Firm* — Morgan, Lewis & Bockius LLP

(57) ABSTRACT

Compounds of formula (I) are agonists of PPARγ, useful for the treatment of respiratory disease; formula (I): wherein $R_1$, $R_2$ or $R_3$ each independently represents halo, cyano, nitro, amino, alkyl, haloalkyl, alkoxy, haloalkoxy, carboxylic acid or an ester or amide thereof; $R_4$ represents hydrogen or alkyl; m, n or p independently represents 0, 1, 2 or 3.

(I)

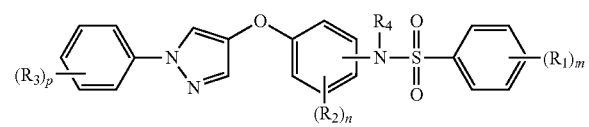

10 Claims, No Drawings

FOREIGN PATENT DOCUMENTS

| | | |
|---|---|---|
| WO | 03/099764 A1 | 12/2003 |
| WO | 2004/016578 A2 | 2/2004 |
| WO | 2004/016601 A1 | 2/2004 |
| WO | 2004/022547 A1 | 3/2004 |
| WO | 2004/032921 A1 | 4/2004 |
| WO | 2004/033412 A1 | 4/2004 |
| WO | 2004/037768 A2 | 5/2004 |
| WO | 2004/037773 A1 | 5/2004 |
| WO | 2004/037807 A2 | 5/2004 |
| WO | 2004/039762 A2 | 5/2004 |
| WO | 2004/039766 A1 | 5/2004 |
| WO | 2004/039827 A1 | 5/2004 |
| WO | 2004/045618 A2 | 6/2004 |
| WO | 2004/046083 A1 | 6/2004 |
| WO | 2004/066920 A2 | 8/2004 |
| WO | 2004/071388 A2 | 8/2004 |
| WO | 2004/080964 A1 | 9/2004 |
| WO | 2004/087142 A1 | 10/2004 |
| WO | 2004/089892 A2 | 10/2004 |
| WO | 2004/108675 A1 | 12/2004 |
| WO | 2004/108676 A1 | 12/2004 |
| WO | 2005/003098 A1 | 1/2005 |
| WO | 2005/026134 | 3/2005 |
| WO | 2005/026134 A1 | 3/2005 |
| WO | 2005/033121 A2 | 4/2005 |
| WO | 2005/034939 A1 | 4/2005 |
| WO | 2005/035502 A1 | 4/2005 |
| WO | 2005/035518 A1 | 4/2005 |
| WO | 2005/040103 A1 | 5/2005 |
| WO | 2005/044787 A1 | 5/2005 |
| WO | 2005/058299 A1 | 6/2005 |
| WO | 2005/058867 A1 | 6/2005 |
| WO | 2005/066140 A1 | 7/2005 |
| WO | 2005/070908 A1 | 8/2005 |
| WO | 2005/077361 A1 | 8/2005 |
| WO | 2005/080313 A2 | 9/2005 |
| WO | 2005/080324 A1 | 9/2005 |
| WO | 2005/090288 A1 | 9/2005 |
| WO | 2005/092840 A1 | 10/2005 |
| WO | 2005/092841 A1 | 10/2005 |
| WO | 2005/092860 A1 | 10/2005 |
| WO | 2005/092861 A1 | 10/2005 |
| WO | 2005/092870 A1 | 10/2005 |
| WO | 2005/092887 A1 | 10/2005 |
| WO | 2005/110359 A1 | 11/2005 |
| WO | 2005/110990 A1 | 11/2005 |
| WO | 2005/111002 A2 | 11/2005 |
| WO | 2005/111005 A1 | 11/2005 |
| WO | 2005/121065 A2 | 12/2005 |
| WO | 2006/014704 A1 | 2/2006 |
| WO | 2006/016245 A1 | 2/2006 |
| WO | 2006/031556 A2 | 3/2006 |
| WO | 2006/032627 A1 | 3/2006 |
| WO | 2006/051373 A1 | 5/2006 |
| WO | 2006/056471 A1 | 6/2006 |

OTHER PUBLICATIONS

Desreumanux et al., "Attenuation of Colon Inflammation through Activators of the Retinoid X Receptor (RXR)/Peroxisome Proliferator-activated Receptor γ (PPARγ) Heterodimer: a basis for new therapeutic strategies," J. Exp. Med., 193(7):827-838 (2001).

Eyles et al., "Immunological responses to nasal delivery of free and encapsulated tetanus toxoid: studies on the effect of vehicle volume," International Journal of Pharmaceutics, 189(1):75-79 (1999).

Feinstein et al., "Peroxisome Proliferator-Activated Receptor-γ Agonists Prevent Experimental Autoimmune Encephalomyelitis," Ann. Neurol., 51(6):694-702 (2002).

Guan et al., "Thiazolidinediones expand body fluid volume through PPARγ stimulation of ENaC-mediated renal salt absorption," Nature Medicine, 11(8):861-866 (2005).

Haffner et al., "Effect of Rosiglitazone Treatment on Nontraditional Markers of Cardiovascular Disease in Patients with Type 2 Diabetes Mellitus," Circulation, 106(6):679-684 (2002).

Halbert et al, "Global burden of COPD: systematic review and meta-analysis," Eur. Respir. J, 28(3):523-532 (2006).

Hetzel et al., "Inhibition of MMP-9 expression by PPARγ activators in human bronchial epithelial cells," Thorax, 58 (9):778-783 (2003).

Lee et al., "PPAR-gamma modulates allergic inflammation through up-regulation of PTEN," FASEB Journal, 19 (8):1033-1035 (2005).

Marx et al., "Antidiabetic PPARγ-Activator Rosiglitazone Reduces MMP-9 Serum Levels in Type 2 Diabetic Patients with Coronary Artery Disease," Arterioscler. Thromb. Vasc. Biol., 23(2):283-288 (2003).

Padeletti et al., "Coexistent chronic obstructive pulmonary disease and heart failure in the elderly," International Journal of Cardiology, 125(2):209-215 (2008).

Reddy et al., "Deactivation of murine alveolar macrophages by peroxisome proliferator-actived receptor-γ ligands," Am. J. Physiol. Lung Cell. Mol. Physiol., 286(3):L613-619 (2004).

Sanchez-Hidalgo et al., "Rosiglitazone, an agonist of peroxisome proliferator-activated receptor gamma, reduces chronic colonic inflammation in rats," Biochemical Pharmacology, 69(12):1733-1744 (2005).

Shiojiri et al., "PPARγ ligands inhibit nitrotyrosine formation and inflammatory mediator expressions in adjuvant-induced rheumatoid arthritis mice," European Journal of Pharmacology, 448(2-3):231-238 (2002).

Stella et al., "Prodrugs: A Chemical Approach to Targeted Drug Delivery," Directed Drug Delivery 247-267 (1985).

Ward et al., "PPARγ ligands, 15-deoxy-Δ12,14-prostaglandin J2 and rosiglitazone regulate human cultured airway smooth muscle proliferation through different mechanisms," British Journal of Pharmacology, 141(3): 517-525 (2004).

Wilman, "Prodrugs in cancer chemotherapy," Biochem. Soc. Trans., 14(2):375-382 (1986).

Zhang et al., "Collecting duct-specific deletion of peroxisome proliferator-activated receptor γ blocks thiazolidinedione-induced fluid retention," Proc. Natl. Acad. Sci. USA, 102(26):9406-9411 (2005).

Medication Guide AVANDIA® rosiglitazone maleate tablets obtained from http://www.fda.gov/cder/foi/ mda/99/21071_Avandia.htm, 2008.

SULFONAMIDE COMPOUNDS FOR THE TREATMENT OF RESPIRATORY DISORDERS

RELATED APPLICATIONS

The present application is a U.S. National Phase Application of International Application No. PCT/GB2009/002951 (filed Dec. 23, 2009) which claims priority to Indian Application No. 3324/CHE/2008 (filed Dec. 30, 2008) which are hereby incorporated by reference in their entirety.

FIELD OF THE INVENTION

The present invention relates to sulfonamide compounds which are agonists of PPARγ, and to the use of such compounds for the treatment of respiratory disease.

BACKGROUND OF THE INVENTION

A broad spectrum of respiratory diseases and disorders has been recognized and many of which have overlapping and interacting etiologies. Two of the most widespread and prevalent of these diseases are chronic obstructive pulmonary disorder (COPD) and asthma. Respiratory diseases have a significant inflammatory component. For example, current therapy for COPD and asthma focuses mainly on the reduction of symptoms using short and long acting bronchodilators either as monotherapies or combinations of long acting β2 agonist bronchodilators with inhaled corticosteroids (ICS).

COPD is a leading cause of morbidity and mortality worldwide with an overall prevalence in adults over 40 years currently estimated at between 9 and 10% (Halbert et al, Eur. Respir. J, 2006, 28(3):523-32). According to the World Health Organization (WHO), about 600 million people suffer from COPD, with some three million dying from the disease each year making it the third leading cause of mortality and fifth leading cause of morbidity in the world by 2020.

Clinical features of COPD include breathlessness, cough and sputum, with chronic airway obstruction and lung hyperinflation as a result of chronic bronchitis and emphysema (dilation of the distal lung airspaces). Chronic bronchial hyperactivity which is prominent in bronchial asthma is also found in COPD. Airway remodeling in COPD leads to persistent and irreversible airway narrowing and mucus hyper secretion. The direct cause of airway narrowing and hyper responsiveness is unknown although it is generally proposed that abnormalities in the airway smooth muscle function results in decreased or impaired relaxation or increased contractility.

COPD is a significant cause of death and disability. Treatment guidelines advocate early detection and implementation of smoking cessation programs to help reduce morbidity and mortality due to the disease. However, early detection and diagnosis has been difficult for a number of reasons.

COPD takes years to develop and smokers often deny any ill effects from smoking, attributing the early warning signs of increased breathlessness as a sign of age. Similarly, acute episodes of bronchitis often are not recognized by the general practitioner as early signs of COPD. Many patients exhibit features of more than one disease (e.g. chronic bronchitis or asthmatic bronchitis) making precise diagnosis a challenge, particularly in early disease. Also, many patients do not seek medical help until they are experiencing more severe symptoms associated with reduced lung function, such as dyspnea, persistent cough, and sputum production. As a consequence, the vast majority of patients are not diagnosed or treated until they are in a more advanced stage of disease.

Despite the recent advances that have been made in understanding the causes of respiratory disorders, they remain notoriously difficult to treat. From the foregoing, it can be seen that a need exists for identifying novel compounds for the prevention and treatment of respiratory disorders such as COPD and asthma.

Currently, COPD treatment focuses mainly on the reduction of symptoms using short and long acting bronchodilators either as monotherapies or combinations of long acting β2 agonist bronchodilators with inhaled corticosteroids (ICS). The disappointing anti-inflammatory data for ICS either alone or in combination with β2 agonists has intensified the search for an effective anti-inflammatory drug for COPD. One hypothesis under investigation is whether novel, demonstrably anti-inflammatory agents can halt or slow function decline characteristic of COPD. Reducing the frequency and severity of exacerbations has become an increasingly important target for COPD therapy as the prognosis for patients following exacerbations is poor. Anti-inflammatory therapy in COPD, and in asthma, is expected to reduce the frequency and severity of exacerbations, improve quality of life and perhaps reduce decline in lung function. Effective anti-inflammatory therapy in COPD may also produce an improvement in lung function.

Peroxisome Proliferation Receptor gamma receptor (PPARγ) agonists are a class of drug which increase sensitivity to glucose in diabetic patients and currently two PPARγ agonists are approved for clinical use in diabetes; Rosiglitazone and Pioglitazone. See Campbell I W, Curr Mol Med. 2005 May; 5(3):349-63. Both of these compounds are thiazolidinediones (TZDs), and are, in practice, administered by the oral route for systemic delivery. Physiological activation of PPARγ is believed to increase the sensitivity of peripheral tissues to insulin, thus facilitating the clearance of glucose from the blood and producing the desired anti-diabetic effect.

Unfortunately, PPARγ agonists also have unwanted cardiovascular effects, including haemodilution, peripheral and pulmonary oedema, and congestive heart failure (CHF). CHF is a complex clinical syndrome characterized by exertional dyspnea, fatigue and, often, peripheral edema resulting from left ventricular dysfunction (LVR). These unwanted effects are also believed to result from activation of PPARγ. In particular, a significant effort has been devoted to investigating the hypothesis that PPARγ agonists disturb the normal maintenance of fluid balance via binding to the PPARγ receptor in the kidney. See Guan et al, Nat Med. 2005; 11(8):861-6 and Zhang et al, Proc Natl Acad Sci USA. 2005 28; 102(26):9406-11. Treatment with PPARγ agonists by the oral route for systemic delivery is also associated with an unwanted increase in body weight.

In addition to their effects on glucose metabolism, a variety of reports have been published which demonstrate the potential of specific PPARγ agonists, such as Rosiglitazone, to exert anti-inflammatory effects. For instance, (i) Rosiglitazone has been reported to exert effects in diabetic patients consistent with an anti-inflammatory effect (Haffner et al, Circulation. 2002 August 6; 106(6):679-84, Marx et al, Arterioscler Thromb Vasc Biol. 2003 February 1; 23(2):283-8); (ii) Rosiglitazone has been reported to exert anti-inflammatory effects in a range of animal models of inflammation, including: carageenan-induced paw oedema (Cuzzocrea et al, Eur J Pharmacol. 2004 January 1; 483(1):79-93), TNBS-induced colitis (Desreumanux et al, J Exp Med. 2001 April 2; 193(7):827-38, Sanchez-Hidalgo et al, Biochem Pharmacol. 2005 June 15; 69(12):1733-44), experimental encephalomyelitis (Feinstein et al, Ann Neurol. 2002 June; 51(6):694-702) collagen-induced (Cuzzocrea et al, Arthritis Rheum. 2003 December; 48(12):3544-56) and adjuvant-induced arthritis (Shiojiri et al, Eur J Pharmacol. 2002 July 19; 448(2-3):231-8), carageenan-induced pleurisy (Cuzzocrea et al, Eur J Pharmacol. 2004 January 1; 483(1):79-93), ovalbumin-induced lung inflammation (Lee et al, FASEB J. 2005 June; 19(8): 1033-5) and LPS-induced lung tissue neutrophilia (Birrell et al, Eur Respir J. 2004 July; 24(1):18-23) and (iii) Rosiglitazone has been reported to exert anti-inflammatory effects in isolated cells, including iNOS expression in murine macrophages (Reddy et al, Am J Physiol Lung Cell Mol Physiol. 2004 March; 286(3):L613-9), TNF□-induced MMP-9 activity in human bronchial epithelial cells (Hetzel et al, Thorax. 2003 September; 58(9):778-83), human airway smooth muscle cell proliferation (Ward et al, Br J Pharmacol. 2004 February; 141(3):517-25) and MMP-9 release by neutrophils (WO 0062766).

Based on observations of anti-inflammatory activity in cells relevant to the lung, the utility of PPARγ agonists in general has been disclosed for the treatment of inflammatory respiratory disorders including asthma, COPD, cystic fibrosis, pulmonary fibrosis (Refer patent applications WO00/53601, WO02/13812 and WO00/62766). These disclosures include administration by both the oral and inhaled routes.

COPD patients are known to be at a higher risk than other clinical populations from congestive heart failure (CHF) (Curkendall et al, Ann Epidemiol, 2006; 16: 63-70, Padeletti et al, Int J Cardiol. 2008; 125(2):209-15) and so it is important that systemic activation of the PPARγ receptors is kept to a minimum in these patients to avoid increasing the likelihood of CHF. Administering respiratory drugs by the inhaled route is one approach to target the lung with an anti-inflammatory agent whilst keeping systemic exposure of the drug low, reducing the likelihood of systemic activity and observation of side effects.

Therefore, taking into account the potential anti-inflammatory utility of PPARγ receptor agonists in the treatment of respiratory disease, and weighing that potential utility against the undesirable side effects of high systemic exposure to this drug class, there is a need for PPARγ receptor agonists that are effective in treating such diseases, have physico-chemical properties rendering them suitable for pulmonary delivery by inhalation, and have low systemic exposure following inhalation.

Systemic exposure of an inhaled drug is generally achieved by two methods. Following oral inhalation of a respiratory drug 10-50% of the dosage delivered by the device (e.g. inhaler or nebuliser) is delivered to the respiratory tract where it can achieve its desired pharmacological action in the lungs. Ultimately, any drug that has not been metabolized by the lungs, is delivered by the lungs to the systemic circulation. Once the active drug is present in the circulation, the clearance rate of the drug from the plasma is critical to its systemic activity. Therefore, a desired property of an inhaled drug for the treatment of lung disease is to have low plasma area under the curve (AUC) relative to the dose administered as this will limit systemic pharmacological activity and thus reduce likelihood of side effects. The suitability of different compounds in this regard can be assessed by determining the plasma AUC following .i.v. dosing at equivalent dosages. Compounds suitable for inhalation for the treatment of lung disease will have a low plasma AUC and compounds likely to have a propensity for systemic side effects will have a higher plasma AUC.

Following oral inhalation of a respiratory drug, the other 50-90% of the inhaled dose is swallowed. Therefore, another method of reducing systemic exposure by an inhaled drug is for the drug to have reduced oral bioavailability (ability of the GI tract to absorb intact drug and deliver it to the circulation). A compound having low oral bioavailability will have significantly lower plasma exposure as measured by plasma AUC following oral dosing than when an equivalent dosage of the same compound is administered by the intravenous (i.v.) route.

DESCRIPTION OF THE INVENTION

In accordance with one aspect, the invention provides a compound of formula (I) or a pharmaceutically acceptable salt thereof

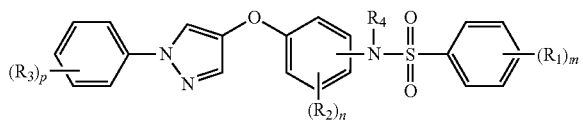

wherein,
$R_1$, $R_2$ or $R_3$ each independently represents halo, cyano, nitro, amino, alkyl, haloalkyl, alkoxy, haloalkoxy, carboxylic acid or an ester or amide thereof;
$R_4$ represents hydrogen or alkyl;
m, n or p independently represents 0, 1, 2 or 3.

The term "compound of formula (I)" or "compound of the invention" as used herein includes any individual stereoisomers of the compound.

In accordance with another aspect, the present application also provides the use of a compound of formula (I) or a pharmaceutically acceptable salt thereof for treatment of, or in the manufacture of a composition for treatment of a respiratory disease such as asthma (mild, moderate or severe), e.g., bronchial, allergic, intrinsic, extrinsic, exercise-induced, drug-induced (including aspirin and NSAID-induced) and dust-induced asthma, steroid resistant asthma, allergic airway syndrome, bronchitis including infectious and eosinophilic bronchitis, chronic obstructive pulmonary disease (COPD), cystic fibrosis, pulmonary fibrosis including cryptogenic fibrosing alveolitis, idiopathic pulmonary fibrosis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension (including pulmonary arterial hypertension); antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza (prophylactic and therapeutic therapy), coronavirus (including SARS) and adenovirus, pulmonary edema, pulmonary embolism, pneumonia, pulmonary sarcoidosis, silicosis, farmer's lung and related diseases; hypersensitivity pneumonitis, respiratory failure, acute respiratory distress syndrome, emphysema, chronic bronchitis, tuberculosis, and lung cancer.

In accordance with another aspect, the present invention provides a method of treating or preventing a respiratory disease such as those listed in the preceding paragraph.

In particular, the methods and compositions of the present invention encompass the prevention and treatment of the respiratory disease such as those listed above in an individual in need of such activity comprising administering to said individual a therapeutically effective amount of a pharmaceutical composition comprising a compound of formula (I), or a pharmaceutically acceptable salt thereof; and one or more pharmaceutically acceptable excipients. In this aspect of the invention, the compound of formula (I) will often be administered by the inhaled route.

In another aspect, the present invention provides a pharmaceutical composition, such as a composition adapted for inhalation by the nose or mouth comprising a compound of the invention, and one or more pharmaceutically acceptable excipients.

To describe the invention, certain terms are defined herein as follows.

As used herein, the term "alkyl" includes both branched and straight-chain saturated or unsaturated aliphatic hydrocarbon groups having from 1 to 10, more preferably 1 to 6, carbon atoms. Non-limiting examples of suitable alkyl groups include methyl, ethyl, n-propyl, isopropyl, n-butyl, and t-butyl.

As used herein, the term "alkoxy" means a chain of carbon atoms and is defined as 'alkyl-O-', wherein alkyl group is as defined above. The chains of carbon atoms of the alkoxy groups described and claimed herein are saturated, may be straight chain or branched. Exemplary alkoxy groups include methoxy, ethoxy, propoxy, isopropoxy and the like.

As used herein, the term, "halo" or "halogen," means fluoro, chloro, bromo or iodo groups.

As used herein, the term "haloalkyl" means an alkyl as defined above wherein one or more hydrogen atoms on the alkyl is replaced by a halo group defined above. Exemplary haloalkyl groups include trifluoromethyl, chloromethyl, flouroethyl, chloroethyl, trilfluoromethy, hexafluoroethyl and the like.

As used herein, the term "haloalkoxy" is haloalkyl-O—, where haloalkyl is as define above. Exemplary haloalkoxy groups include trifluoromethoxy, chloromethoxy, flouroethoxy, chloroethoxy, trilfluoromethoxy, hexafluoroethoxy and the like.

As used herein, the term, "carboxylic acid or its esters or its amides" means ester or amide derivatives of carboxylic acids. Exemplary ester and amide derivatives include $CONH_2$, $CONHMe$, $CONMe_2$, $CONHEt$, $CONEt_2$, $CONHPh$, $CON(OMe)Me$, $COOH$, $COOR$ "wherein R" represents alkyl or phenylalkyl such as benzyl.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The terms "treatment," "treating," "treat," and the like are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a human, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The term "therapeutically effective amount" refers to the amount of a drug or pharmaceutical agent that will elicit the biological or medical response of a tissue, system or patient that is being sought.

In the compounds of the invention:

Substituents $R_1$, $R_2$ $R_3$, when present, may be selected independently from, for example, methyl, fluoro, chloro, trifluoromethyl, methoxy, and trifluoromethoxy.

$R_4$ may be, for example, hydrogen or methyl

In some embodiments m, n and p are independently 0, 1 or 2.

Specific examples of compounds of the present invention include the following, and pharmaceutically acceptable salts thereof:

---

Compounds and IUPAC Name

---

2,4-Dichloro-N-[4-(1-p-tolyl-1H-pyrazol-4-yloxy)-phenyl]-benzenesulfonamide

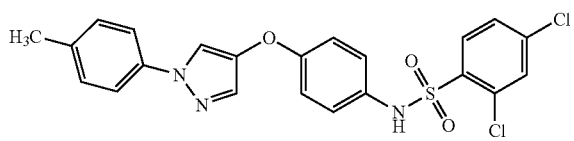

2,4-Dichloro-N-{3-chloro-4-[1-(4-chloro-3-trifluoromethyl-phenyl)-1H-pyrazol-4-yloxy]-phenyl}-benzenesulfonamide

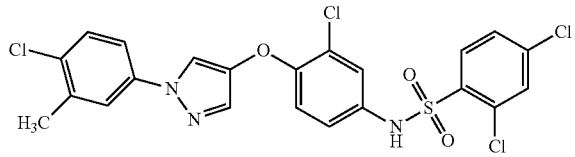

2,4-Dichloro-N-{3,5-dichloro-4-[1-(2,4-difluoro-phenyl)-1H-pyrazol-4-yloxy]-phenyl}-benzenesulfonamide

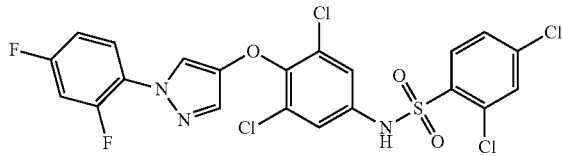

2,4-Dichloro-N-{3,5-dichloro-4-[1-(4-fluoro-phenyl)-1H-pyrazol-4-yloxy]-phenyl}-benzenesulfonamide

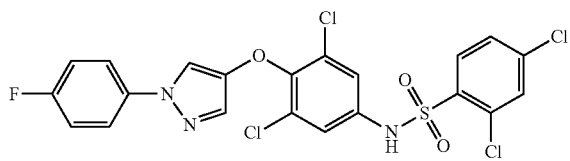

| Compounds and IUPAC Name |
|---|
| 2,4-Dichloro-N-{3-chloro-4-[1-(4-fluoro-phenyl)-1H-pyrazol-4-yloxy]-phenyl}-benzenesulfonamide |
| 2,4-Dichloro-N-{3-chloro-4-[1-(4-chloro-phenyl)-1H-pyrazol-4-yloxy]-phenyl}-benzenesulfonamide |
| 2,4-Dichloro-N-{3-chloro-4-[1-(3-chloro-4-fluoro-phenyl)-1H-pyrazol-4-yloxy]-phenyl}-benzenesulfonamide |
| N-{3-Chloro-4-[1-(4-fluoro-phenyl)-1H-pyrazol-4-yloxy]-phenyl}-4-methyl-benzenesulfonamide |
| 2,4-Dichloro-N-{4-[1-(4-fluoro-phenyl)-1H-pyrazol-4-yloxy]-3-methyl-phenyl}-benzenesulfonamide |
| 2,4-Dichloro-N-{4-[1-(2,4-dimethyl-phenyl)-1H-pyrazol-4-yloxy]-phenyl}-benzenesulfonamide |
| 4-Methyl-N-[4-(1-p-tolyl-1H-pyrazol-4-yloxy)-phenyl]-benzenesulfonamide |
| N-{3-Chloro-4-[1-(4-fluoro-phenyl)-1H-pyrazol-4-yloxy]-phenyl}-benzenesulfonamide |
| 2,4-Dichloro-N-[3-chloro-4-(1-phenyl-1H-pyrazol-4-yloxy)-phenyl]-benzenesulfonamide |
| N-{4-[1-(2,4-Dimethyl-phenyl)-1H-pyrazol-4-yloxy]-phenyl}-4-methyl-benzenesulfonamide |
| N-{3-Chloro-4-[1-(2,4-dimethyl-phenyl)-1H-pyrazol-4-yloxy]-phenyl}-4-methyl-benzenesulfonamide |

As used herein, the terms "pharmaceutically acceptable" salt or "pharmacologically acceptable" salt refers generally to a salt or complex of the compound or compounds in which the compound can be either anionic or cationic, and have associated with it a counter cation or anion, respectively that is generally considered suitable for human or animal consumption. For example, a pharmaceutically acceptable salt can refer to a salt of a compound disclosed herein that forms upon reaction or complexation with an acid whose anion is generally considered suitable for human or animal consumption. In this aspect, pharmacologically acceptable salts include salts with organic acids or inorganic acids. Examples of pharmacologically acceptable salts include, but are not limited to, Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituents are selected from nitro, amino, alkyl, alkenyl, alkynyl, ammonium or substituted ammonium salts and aluminum salts; sulphates, nitrates, phosphates, perchlorates, borates, hydrohalides, acetates, tartrates, maleates, citrates, succinates, oxalates, palmoates, methanesulphonates, benzoates, salicylates, hydroxynaphthoates, benzenesulfonates, ascorbates, glycerophosphates, or ketoglutarates.

The compounds can be formulated and administered in a prodrug form. In general, prodrugs comprise functional derivatives of the claimed compounds which are capable of being enzymatically activated or converted into the more active parent form. Thus, in the treatment methods of the present invention, the term "administering" encompasses the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in Wihnan, 14 *Biochem. Soc. Trans.* 375-82 (1986); Stella et al., Prodrugs: A Chemical Approach to Targeted Drug Delivery, in *Directed Drug Delivery* 247-67 (1985).

As used herein, the terms "Prodrugs" of the compounds disclosed herein refers to species that have chemically- or metabolically-cleavable groups wherein, under physiological conditions, the species become, provide, release, or are transformed into the compounds disclosed herein. In this manner, prodrugs can release the pharmaceutically in vivo active compounds disclosed herein. For example, prodrugs of present invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine or other 5-fluorouridine prodrugs which may be converted into the more active species, and the like. In another aspect, prodrugs of present invention include, but are not limited to derivatives of carboxylic acid, sulfonamide, amine, hydroxyl, and the like, including other functional groups and including any combination thereof.

The compounds of the invention are agonists of the PPAR gamma receptor.

The invention also provides a compound of the invention for use for the treatment or prevention of a respiratory disease such as asthma or Chronic Obstructive Pulmonary Disease (COPD). For treatment of respiratory disease, the compound of the invention may be administered by, for example, the inhaled route.

In another aspect, the present invention provides a pharmaceutical composition comprising a compound of the invention and one or more pharmaceutically acceptable excipients. Preferred pharmaceutical compositions include those adapted for administration by inhalation through the nose or, especially, the mouth.

The general advantages of inhalation of PPARγ agonists as a route for treatment of respiratory disease have been described in the introduction above. An additional advantage of delivering an anti-inflammatory therapy by the inhaled route for the treatment of respiratory disease is that it can be administered in combination with an inhaled bronchodilator drug. Bronchodilator therapies are first line treatments for chronic inflammatory diseases such as asthma and COPD and provide rapid symptomatic relief. In contrast, anti-inflammatories can have less pronounced immediate benefits which can hinder patient compliance, despite offering significant clinical benefits following chronic therapy. Inhaled combination therapy of an anti-inflammatory with a bronchodilator can improve compliance and this has been found with β2 adrenergic agonist/glucocorticoid combination products such as Advair®/Seretide® (salmeterol xinafoate/fluticasone propionate) and Symbicort® (formoterol fumarate/Budesonide).

As used herein, the phrases "combination therapy", "co-administration", "co-administering", "administration with", "administering", "combination", or "co-therapy", when referring to use of compounds of Formula (I) and a respiratory disorder treatment agent other than a PPARγ agonist, are intended to embrace administration of each agent in a sequential manner in a regimen that will provide beneficial effects of the drug combination, and is intended as well to embrace co-administration of these agents in a substantially simultaneous manner. Thus, compounds of Formula (I) and a respiratory disorder treatment agent other than a PPARγ agonist may be administered in one inhalable therapeutic dosage form, such as or in two or more separate therapeutic dosage forms, of which at least that containing a compound of Formula (I) is inhalable.

Sequential administration of such treatments encompasses both relatively short and relatively long periods between the administration of each of the drugs of the present method. However, for purposes of the present invention, the second drug is administered while the first drug is still having an efficacious effect on the subject. Thus, the present invention takes advantage of the fact that the simultaneous presence of the combination of a compound of Formula (I) and a respiratory disorder treatment agent other than a PPARγ agonist in a subject has a greater efficacy than the administration of either agent alone.

In some embodiments, the second of the two drugs is to be given to the subject within the therapeutic response time of the first drug to be administered. For example, the present invention encompasses administration of a compound of Formula (I) to the subject and the later administration of a respiratory disorder treatment agent, as long as the respiratory disorder treatment agent is administered to the subject while the compound of Formula (I) is still present in the subject at a level, which in combination with the level of the respiratory disorder treatment agent is therapeutically effective, and vice versa.

As used herein, the terms "therapeutic response time" mean the duration of time that a compound is present or detectable within a subject's body.

As used herein, the term "monotherapy" is intended to embrace administration of a compound of Formula (I) to a subject suffering from a respiratory disorders or respiratory disorder-related complication as a single therapeutic treatment without an additional therapeutic treatment comprising a respiratory disorder treatment agent other than a PPARγ agonist. However, the compound of Formula (I) may still be administered in multiple dosage forms. Thus, the compound of Formula (I) may be administered in one or more inhaled powder or aerosol doses.

In some embodiments, combination therapy in accordance with the invention may include the inhaled administration of a compound of Formula (I) in combination with bronchodilator medicines. As used herein, the term "bronchodilator" means a medicament that relaxes bronchial muscle resulting in expansion of the bronchial air passages. Included as bronchodilators are, without limitation, β2 adrenergic agonists, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, picumeterol, BI 1744 CL, GSK159797, GSK59790, GSK159802, GSK642444, GSK678007, GSK96108, clenbuterol, procaterol, bitolterol, and brodxaterol, TA-2005 and also compounds of EP1440966, JP05025045, WO93/18007, WO99/64035, US2002/0055651, US2005/0133417, US2005/5159448, WO00/075114, WO01/42193, WO01/83462, WO02/66422, WO02/70490, WO02/76933, WO03/24439, WO03/42160, WO03/42164, WO03/72539, WO03/91204, WO03/99764, WO04/16578, WO04/016601, WO04/22547, WO04/32921, WO04/33412, WO04/37768, WO04/37773, WO04/3 7807, WO04/39762, WO04/39766, WO04/45618, WO04/46083, WO04/71388, WO04/80964, EP1460064, WO04/087142, WO04/89892, EP01477167, US2004/0242622, US2004/0229904, WO04/108675, WO04/108676, WO05/033121, WO05/040103, WO05/044787, WO04/071388, WO05/058299, WO05/058867, WO05/065650, WO05/066140, WO05/070908, WO05/092840, WO05/092841, WO05/092860, WO05/092887, WO05/092861, WO05/090288, WO05/092087, WO05/080324, WO05/080313, US20050182091, US20050171147, WO05/092870, WO05/077361, DE10258695, WO05/111002, WO05/111005, WO05/110990, US2005/0272769 WO05/110359, WO05/121065, US2006/0019991, WO06/016245, WO06/014704, WO06/031556, WO06/032627, US2006/0106075, US2006/0106213, WO06/051373, WO06/056471; and anticholinergic bronchodilators, such as ipratropium bromide, tiotropium, tiotropium bromide (Spiriva®), glycopyrollate, NVA237, LAS34273, GSK656398, GSK233705, GSK 573719, LAS35201, QAT370 and oxytropium bromide. Other bronchodilators may include TA 2005 (i.e., 8-hydroxy-5-(1-hydroxy-2-2((2-(4-methoxy-phenyl)-1-methylethyl) amino)ethyl)-2(1H)-quinolinone) (for instance as the monohydrochloride), as well as anti-histamines (e.g., terfenadine).

In some embodiments, combination therapy may also involve the inhaled administration of a compound of Formula (I) in combination with other anti-inflammatory drugs, including but not limited to corticosteroids such as beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocoritisone, desoxycorticosterone, rofleponide, etiprednnol dicloacetate and the like. Steroid drugs may additionally include steroids in clinical or pre-clinical development for respiratory diseases such as GW-685698, GW-799943, NCX-1010, NCX-1020, NO-dexamethasone, PL-2146, NS-126 (formerly ST-126) and compounds referred to in international patent applications WO02/12265, WO02/12266, WO02/100879, WO03/062259, WO03/048181 and WO03/042229 WO02/88167, WO02/00679, WO03/35668, WO03/62259, WO03/64445, WO03/72592, WO04/39827 and WO04/66920. Steroid drugs may also additionally include next generation molecules in development with reduced side effect profiles such as selective glucocorticoid receptor agonists (SEGRAs), including ZK-216348 and compounds referred to in international patent applications WO-00/032585, WO-00/0210143, WO-2005/034939, WO-2005/003098, WO-2005/035518 and WO-2005/035502 and functional equivalents and functional derivatives thereof.

The combinations of the invention may optionally comprise one or more additional active substances which are known to be useful in the treatment of respiratory disorders such as phosphodiesterase (PDE) 4 inhibitors (such as roflumilast), PDE5 inhibitors, PDE7 inhibitors, leukotriene D4 inhibitors, leukotriene B4 inhibitors, inhibitors of egfr-kinase, p38 MAP kinase inhibitors, NF-kB pathway inhibitors such as IkK inhibitors, A2A adenosine receptor agonists, TNFalpha signalling inhibitors (such as ligand binding agents, receptor antagonists), Interleukin-1 signalling inhibitors, CRTH2 receptor antagonists, protease inhibitors (such as neutrophil elastase inhibitors, MMP inhibitors, Cathepsin inhibitors), IL-8 signalling molecules, CXCR1 inhibitors, CXCR2 inhibitors, iNOS modulators, anti-oxidants (including N-acetylcysteine and superoxide dismutase mimetics), HMG-CoA reductase inhibitors (statins); for example rosuvastatin, mevastatin, lovastatin, simvastatin, pravastatin and fluvastatin; Mucus regulators such as INS-37217, diquafosol, sibenadet, CS-003, talnetant, DNK-333, MSI-1956, gefitinib; and/or NK-1 receptor antagonists.

In one aspect, the invention provides for the use of inhaled administration of a compound of Formula (I) in combination with other anti-inflammatory drugs and bronchodilator drug combinations (i.e. triple combination product), including but not limited to salmeterol xinafoate/fluticasone propionate (Advair/Seretide®), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, arformoterol tartrate/ciclesonide.

In another aspect, the invention provides for the use of inhaled administration of a compound of Formula (I) in combination with other bronchodilator drug combinations, particularly B2 agonist/M3 antagonist combinations (i.e. triple combination product), including but not limited to salmeterol xinafoate/tiotropium bromide, formoterol fumarate/tiotropium bromide, BI 1744 CL/tiotropium bromide, indacaterol/NVA237, indacaterol/QAT-370, formoterol/LAS34273, GSK159797/GSK 573719, GSK159802/GSK 573719, GSK642444/GSK 573719, GSK159797/GSK 233705, GSK159802/GSK 233705, GSK642444/GSK 233705, and compounds which possess both B2 agonist and M3 antagonist activity in the same molecule (dual functionality) such as GSK 961081.

The compounds of the formula (I) of the present invention would be useful, for example, to reduce such respiratory disorder symptoms as, for example, coughing, inflammation, congestion, dyspnea, wheezing, hyperventilation, difficulty breathing, bronchospasm, and bronchoconstriction in a subject suffering from such symptoms. The compounds of the present invention would also be useful to prevent the occurrence of such symptoms.

As used herein, the terms "therapeutic response time" mean the duration of time that a compound is present or detectable within a subject's body.

The compounds described herein are typically administered in admixture with one or more pharmaceutical acceptable excipients or carriers in the form of a pharmaceutical composition. A "composition" may contain one compound or a mixture of compounds. A "pharmaceutical composition" is any composition useful or potentially useful in producing physiological response in a subject to which such pharmaceutical composition is administered.

The term "pharmaceutically acceptable," with respect to an excipient, is used to define non-toxic substances generally suitable for use in human or animal pharmaceutical products. The pharmaceutical composition may be in the forms normally employed, such as tablets, capsules, powders, syrups, solutions, suspensions and the like, may contain flavorants, sweeteners, etc., in suitable solid or liquid carriers or diluents, or in suitable sterile media to form injectable solutions or suspensions. Such compositions typically contain from 0.1 to 50%, preferably 1 to 20% by weight of active compound, the remainder of the composition being pharmaceutically acceptable carriers, diluents or solvents.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the active ingredient can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the active ingredient can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

Tablets, dragees or capsules having talc and/or a carbohydrate carried binder or the like are particularly suitable for any oral application. Preferably, carriers for tablets, dragees or capsules include lactose, corn starch and/or potato starch. A syrup or elixir can be used in cases where a sweetened vehicle can be employed.

Dosage forms for nasal or inhaled administration may conveniently be formulated as aerosols, solutions, suspensions, gels or dry powders.

For nasal administration, the preparation may contain the active ingredient of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabens.

For compositions suitable and/or adapted for inhaled administration, it is preferred that the compound of the invention is in a particle-size-reduced form, and more preferably the size-reduced form is obtained or obtainable by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or nonaqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC) also referred to as a hydrofluoroalkane (HFA). Suitable HFC propellants include 1,1,1,2,3,3,3-heptafluoropropane (HFA 227) and 1,1,1,2-tetrafluoroethane (HFA 134a). The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or salt thereof (preferably in particle-size-reduced form, e.g. in micronised form), and optionally a performance modifier such as L-leucine or another amino acid, cellobiose octaacetate and/or metals salts of stearic acid such as magnesium or calcium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometres) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

The compounds of the invention thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation.

The housing has at least one finger-operable side lever which is movable inwardly with respect to the housing to cam the container upwardly in the housing to cause the pump to compress and pump a metered dose of the formulation out of a pump stem through a nasal nozzle of the housing.

For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

The pharmaceutically acceptable compounds the invention can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

An embodiment of the present invention provides preparation of the novel compounds of formula (I) according to the procedure of the following schemes, using appropriate materials. Those skilled in the art will readily understand that known variations of the conditions and processes of the following preparative procedures can be used to prepare these compounds. Moreover, by utilizing the procedures described in detail, one of ordinary skill in the art can readily prepare additional compounds of the present invention claimed herein. All temperatures are in degrees Celsius unless otherwise noted.

General Process:

The following reaction scheme describes the process for the preparation of a compound of formula (I).

Scheme 1:

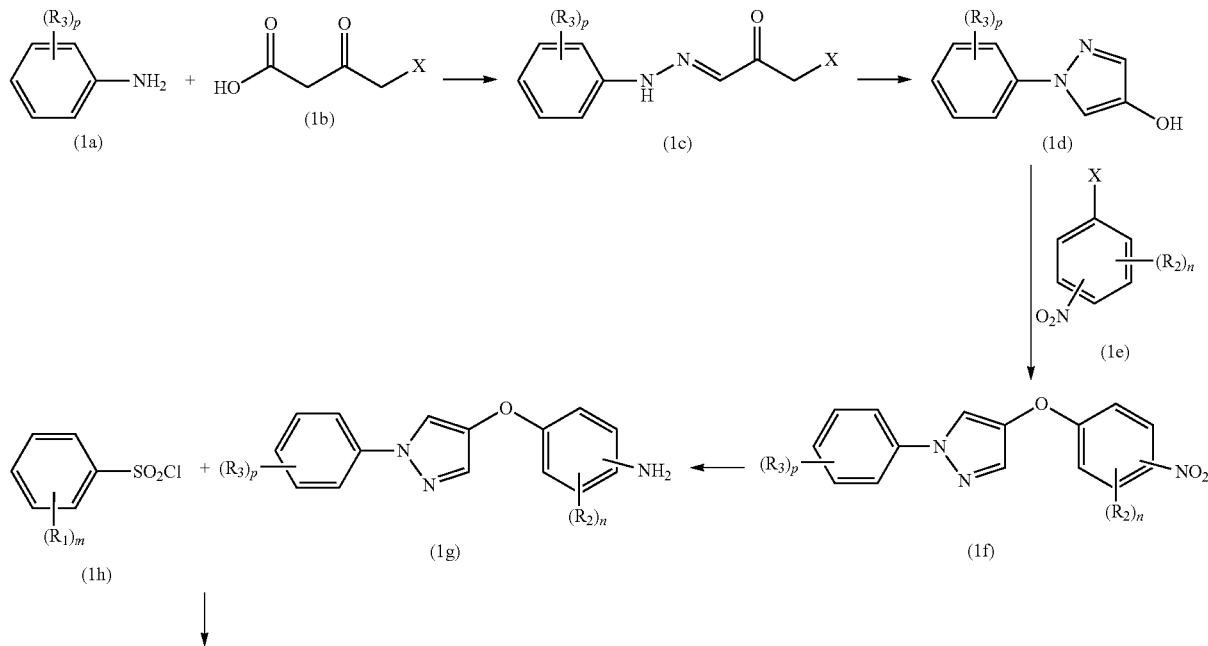

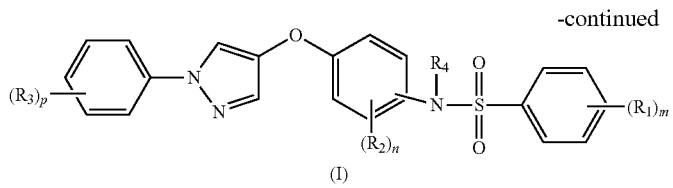

i Reacting the compound of formula (1a), wherein $R_3$ and p, are same as explained in formula (I), with (1b) wherein X represents halogen, hydroxyl or its derivatives (OMs, OTs, OTf and the like) or silyloxy, in presence of solvents such as, but not limited to water, alcohols, acetone, THF, dioxane or their mixture in any ratio, and the like, with appropriate metal nitrite and organic nitrite/nitrate such as but not limited to sodium nitrite, potassium nitrite, isoamyl nitrite/nitrate and mixture thereof, in presence of base such as, but not limited to sodium acetate, potassium acetate, calcium acetate, KOH, NaOH, LiOH, Ca(OH)$_2$, NaHCO$_3$, Na$_2$CO$_3$, K$_2$CO$_3$ or mixture thereof and the like, at temperature in the range of −78° C. to reflux temperature of solvent, for a period in the range of 10 minutes to 7 days, to obtain a compound of formula (1c).

ii Reacting the compound of formula (1c), in presence of organic or inorganic base or acid such as, but not limited to TEA, pyridine, DMAP, DIPEA, LiOH, NaOH, KOH, KHCO$_3$, NaHCO$_3$, K$_2$CO$_3$, Na$_2$CO$_3$, sodium-t-butoxide, potassium-t-butoxide, n-BuLi, t-BuLi, or mixture thereof, or, HCl, H$_2$SO4, p-TSA or mixture thereof and the like, in presence of organic or inorganic solvent such as, but not limited to, methanol, ethanol, propanol, isopropanol, THF, dioxane, water, or, their mixture and the like, at a temperature in the range of −78° C. to reflux temperature of solvent, for a period in the range of 10 minutes to 7 days, to obtain a compound of formula (1d).

iii Reacting the compound of formula (1d) with formula (1e) wherein X represents halogens, hydroxyl or its derivatives (OMs, OTs, OTf and the like) or silyloxy, in presence or absence of organic or inorganic bases such as but not limited to TEA, pyridine, DMAP, DIPEA, NaOH, KOH, CaOH, K$_2$CO$_3$, Na$_2$CO$_3$, NaHCO$_3$, KHCO$_3$, sodium-t-butoxide, potassium-t-butoxide, n-BuLi, t-BuLi, or mixture thereof, and the like, in presence or absence of solvent such as, but not limited to dimethyl formamide, dichloromethane, ethyl acetate, acetonitrile, methanol, ethanol, IPA, acetone, THF, dioxane, water or mixture thereof and the like, at a temperature in the range of −78° C. to reflux temperature of solvent, for a period in the range of 10 minutes to 7 days, to obtain a compound of formula (1f).

iv Hydrogenating the compound of formula (1f) with a transition metal catalyst such as, but not limited to Fe, Co, Pd/C, Ra—Ni, Pt, Ru, Rh, or their mixture and the like, under the pressure (1 atm to 100 atm) of hydrogen gas or with a metal-acid or metal-base reagents such as but not limited to Fe/HCl, Zn/HCl, Sn/HCl, Fe/AcOH, Zn/AcOH, SnCl$_2$, Al/NaOH, Zn/NaOH, ammonium formate or their mixture and the like in absence or presence of hydrogen gas in presence or absence of solvent such as but not limited to alcohols such as methanol, ethanol, IPA, t-BuOH, acetic acid, propionic acid, THF, DMF, DMSO, EtOAc, acetone, water, acetonitrile or their mixture and the like, at a temperature range of −78° C. to reflux temperature of solvent, for a period in the range of 10 minutes to 7 days, to obtain a compound of formula (1g).

v Reacting the compound of formula (1g) with formula (1h), in presence of organic or inorganic base such as, but not limited to, pyridine, triethyl amine, dimethyl amino pyridine, LiOH, NaOH, KOH, Ca(OH)$_2$, K$_2$CO$_3$, Na$_2$CO$_3$, NaHCO$_3$, KHCO$_3$, sodium-t-butoxide, potassium-t-butoxide, n-BuLi, t-BuLi, or mixture thereof, and the like, in presence of solvent such as but not limited to chloroform, dichloromethane, dichloroethance, dioxane, THF, DMF, DMSO, EtOAc, acetone, acetonitrile, methanol, ethanol, IPA, t-BuOH, water, or mixture thereof, and the like, at a temperature range of −78° C. to reflux temperature of solvent, for a period in the range of 10 minutes to 7 days, to obtain a compound of formula (I).

General Synthetic Procedures

All eluents for column or thin layer chromatography were prepared and reported as volume:volume (v:v) solutions. The quantities of solvents and reagents used for reaction work-up or product isolation are those typically used by one trained in the art of organic chemical synthesis, and the quantity of these solvents and reagents used is determined based upon synthetic experience and appropriateness to the specific reaction. For example: 1) crushed ice quantity typically ranged from about 10-1000 grams depending on reaction scale; 2) silica gel quantity used in column chromatography depended on material quantity, complexity of mixture, and size of chromatography column employed and typically ranged from about 5-1000 grams; 3) extraction solvent volume ranged from about 10-500 mL depending on reaction size; 4) washes employed in compound isolation ranged from about 10-100 mL of solvent or aqueous reagent depending on scale of reaction; and 5) drying reagent amounts (potassium carbonate, sodium carbonate, sodium sulfate, magnesium sulfate, and the like) typically ranged from about 5-100 grams depending on the amount of solvent to be dried and its water content.

The following acronyms, abbreviations, terms and definitions have been used throughout the experimental section.

ACRONYMS OR ABBREVIATIONS

THF (tetrahydrofuran), HCl (hydrochloride), K$_2$CO$_3$ (potassium carbonate), Na$_2$SO$_4$ (sodium sulphate), CDCl$_3$ (chloroform-d), NaOH (sodium hydroxide), Pd/C (Palladium on Carbon), Fe (Iron), NaHCO$_3$ (Sodium bicarbonate), TLC (thin layer chromatography), mol (mole), mmol (milli mole), mL (milliliters), M.Pt. (melting point), rt (room temperature), aq (aqueous), min (minute), h (hr, hour), g (grams), atm (atmosphere), conc. (concentrated), MS (mass spectroscopy/spectrometry), HPLC (high performance liquid chromatography), IR (infrared), NMR (nuclear magnetic resonance).

NMR Abbreviations:
br (broad), apt (apparent), s (singlet), d (doublet), t (triplet), q (quartet), dq (doublet of quartets), dd (doublet of doublets), dt (doublet of triplets), m (multiplet).

EXAMPLE 1

Synthesis of 2,4-dichloro-N-[4-(1-p-tolyl-1H-pyrazol-4-yloxy)-phenyl]benzene sulfonamide Step 1: Preparation of (p-Tolyl-hydrazono)-acetyl chloride

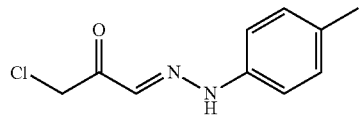

4-Methyl aniline (4 g, 37.38 mmol) was suspended in water: HCl (2:1); 30 ml. Aqueous solution of sodium nitrite (2.57 g, 37.38 mmol) was added at 0°-5° C. over a period of 30 minutes. Subsequently, aqueous solution of chloroacetoacetic acid (6.63 g, 48.59 mmol) was added followed by aqueous solution of sodium acetate (6.13 g, 74.76 mmol).

Reaction mixture was stirred at 20-35° C. for about half an hour. The precipitate, (p-Tolyl-hydrazono)-acetyl chloride was filtered off and washed with cold water and petroleum ether and dried over vacuum. Amount: 4 g
Yield: 51% (crude)

Step 2: Preparation of 1-p-tolyl-1H-pyrazol-4-ol

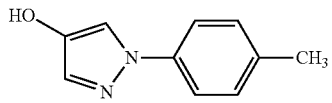

(p-Tolyl-hydrazono)-acetyl chloride (4.0 g, 19.04 mmol) was then taken in methanol and sodium hydroxide (1.52 g, 38.0 mmol) was added. And the reaction mixture was stirred for 2.5 hours. Methanol was removed and residue was taken up in water and pH was made 3 by adding dilute HCl. The solid was filtered off through on Buckner funnel, washed with cold water, dried under vacuum, and further washed with petroleum ether and dried under vacuum.
Amount: 2.5 g
Yield: 76% (pure)

Step 3: Preparation of 4-(4-Nitro-phenoxy)-1-p-tolyl-1H-pyrazole

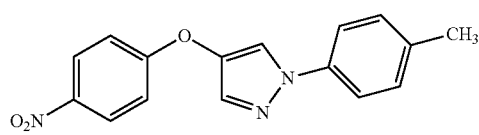 [SMILES: Cc1ccc(-n2cc(Oc3ccc([N+](=O)[O-])cc3)cn2)cc1]

1-p-Tolyl-1H-pyrazol-4-ol (1.0 g, 5.75 mmol) in dimethylformamide was added to the cold slurry of sodium hydride (344 mg, 8.61 mmol). Reaction mixture was stirred for 0.5 hour followed by addition of 4-fluoro nitro benzene (810 mg, 5.74 mmol) in cold condition. Reaction mixture was stirred at 20-35° C. for 20 minutes. Water was then added to quench the reaction. The aqueous layer was extracted with diethylether and the combined organic layer was washed with brine solution and dried over anhydrous $Na_2SO_4$. The solvent was evaporated under vacuum at 40° C. and the product was purified by column chromatography using mixture of petroleum ether and ethyl acetate.
Amount: 1.1 g
Yield: 65% (pure)

Step 4: Preparation of 4-(1-p-tolyl-1H-pyrazol-4-yloxy)-phenylamine

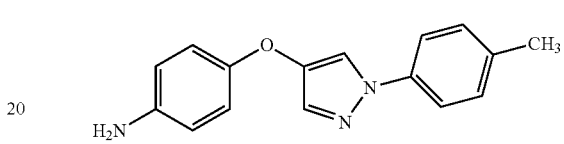

4-(4-Nitro-phenoxy)-1-p-tolyl-1H-pyrazole (600 mg, 2.03 mml) was taken in ethanol and iron powder (1.13 g, 20.33 mmol) was added and stirred at 20-35° C. for 6 hours. Iron powder was removed and ethanol was evaporated under vacuum. Residue was taken up in water and pH was adjusted to 7 using saturated $NaHCO_3$ solution. The aqueous layer was extracted with ethyl acetate, was washed with brine solution and dried over anhydrous $Na_2SO_4$. The solvent was evaporated under vacuum at 50° C. and the product was dried in high vacuum.
Amount: 600 mg
Yield: 100% (crude).

Alternatively, reduction of nitro compound was also done with 10% palladium carbon in methanol solvent under hydrogen atmosphere.

Step 5: Preparation of 2,4-dichloro-N-[4-(1-p-tolyl-1H-pyrazol-4-yloxy)-phenyl]benzene sulfonamide

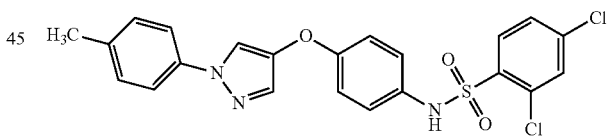

4-(1-p-Tolyl-1H-pyrazol-4-yloxy)-phenylamine (100 mg, 0754 mmol), 2,4 Dichloro-benzenesulfonyl chloride (92 mg, 0.754 mmol) was taken in chloroform and 0.2 ml of pyridine was added and the reaction mixture was stirred at 20-35° C. for 3 and half an hours. Chloroform was removed under vacuum and the product was purified though column chromatography using petroleum ether and ethyl acetate.
Amount: 60 mg
Yield: 34% (pure)
M.P: 152-153
$^1$H NMR (CDCl$_3$): δ: 7.87 (d, 1H, J=8.8 Hz); 7.70 (s, 1H); 7.53 (d, 1H, J=1.6 Hz); 7.51 (s, 1H); 7.48 (s, 2H); 7.31 (dd, 1H, J=8.8 Hz, J2=2.4 Hz); 7.24 (d, 2H, J=8.4 Hz); 7.05 (d, 2H, J=8.8 Hz); 6.93 (d, 2H, J=8.8 Hz, 6.88 (bs, 1H(–NH), 2.15 (s, 3H)
MS: 474 (M$^+$).
IR cm$^{-1}$:3126, 1500, 1186.

The following Examples 2-15 were prepared by using procedures analogous to that of Example 1 from appropriate starting material and by using appropriate substituted phenyl sulphonyl chlorides compound in step-5.

| Example No. | Compounds and IUPAC Name | Analytical Data |
|---|---|---|
| 2 | 2,4-Dichloro-N-{3-chloro-4-[1-(4-chloro-3-trifluoromethyl-phenyl)-1H-pyrazol-4-yloxy]-phenyl}-benzenesulfonamide | $^1$H NMR (CDCl$_3$): δ: 7.97 (d, 1H, J = 2.8 Hz) 7.93 (d, 1H, J = 8.4 Hz); 7.73 (d, 2H, J = 9.2 Hz); 7.58 (d, 2H, J = 8.8 Hz); 7.55 (m, 1H); 7.35 (dd, 1H, J1 = 8.4 Hz, J2 = 2 Hz); 6.98-6.94 (m, 4H). MS: 526 (M$^+$ + 1) IR: 3442, 1599, 1500, 1323 M. Pt. °C.: 66-68 |
| 3 | 2,4-Dichloro-N-{3,5-dichloro-4-[1-(2,4-difluoro-phenyl)-1H-pyrazol-4-yloxy]-phenyl}-benzenesulfonamide | $^1$H NMR (CDCl$_3$): δ: 7.90 (d, 1H, J = 8.4 Hz); 7.80 (m, 1H); 7.61 (d, 2H, J = 1.6 Hz); 7.41-7.39 (m, 2H); 7.17 (s, 2H); 699-6.92 (m, 2H) MS: 566 (M$^+$ + 2) IR: 3257, 1571, 1517, 1168 M. Pt. °C.: 93-95 |
| 4 | 2,4-Dichloro-N-{3,5-dichloro-4-[1-(4-fluoro-phenyl)-1H-pyrazol-4-yloxy]-phenyl}-benzenesulfonamide | $^1$H NMR (CDCl$_3$): δ: 8.01 (d, 1H, J = 8.2 Hz); 7.57 (d, 1H, J = 2 Hz); 7.55 (dd, 2H, J1 = 9.2 Hz), J2 = 5.2 Hz); 7.50 (s, 1H); 7.41 (dd, 1H, J1 = 8.4 Hz, J2 = 2 Hz); 7.38 (s, 1H); 7.17 (s, 2H); 7.12 (d, 2H, J = 8 Hz); 7.08 (m, 1H) MS: 547 (M$^+$ + 1) IR: 3207, 2925, 1575, 1166 M. Pt. °C.: 160-161 |
| 5 | 2,4-Dichloro-N-{3-chloro-4-[1-(4-fluoro-phenyl)-1H-pyrazol-4-yloxy]-phenyl}-benzenesulfonamide | $^1$H NMR (CDCl$_3$): δ: 7.92 (d, 1H, J = 8.4 Hz); 7.69 (s, 1H); 7.60-7.57 (m, 3H); 7.05 (s, 1H); 7.34 (dd, 1H, J1 = 8.8 Hz, J2 = 2 Hz); 7.24 (d, 1H, J = 2 Hz); 7.14 (t, 2H, J = 8.4 Hz); 6.96-6.90 (m, 3H) MS: 529 (M$^+$) IR: 3275, 1573, 1491, 1167 M. Pt. °C.: 129-129 |
| 6 | 2,4-Dichloro-N-{3-chloro-4-[1-(4-chloro-phenyl)-1H-pyrazol-4-yloxy]-phenyl}-benzenesulfonamide | $^1$H NMR (CDCl$_3$): δ: 7.92 (d, 1H, J = 8.4 Hz); 7.71 (s, 1H); 7.57-7.54 (m, 3H); 7.51 (s, 1H); 7.41 (d, 2H, J = 7.6 Hz); 7.35 (dd, 1H, J1 = 8.2 Hz, J2 = 2 Hz); 7.24 (s, 1H); 6.96-6.90 (m, 3H) MS: 529 (M$^+$) IR: 3375, 1573, 1491, 1167 M. Pt. °C.: 150 |
| 7 | 2,4-Dichloro-N-{3-chloro-4-[1-(3-chloro-4-fluoro-phenyl)-1H-pyrazol-4-yloxy]-phenyl}-benzenesulfonamide | $^1$H NMR (CDCl$_3$): δ: 7.92 (d, 1H, J = 8.4 Hz); 7.71 (dd, 1H, J1 = 6 Hz, J2 = 2.8 Hz); 7.67 (s, 1H); 7.55 (d, 1H, J = 2.4 Hz); 7.50 (s, 1H); 7.48 (m, 1H); 7.35 (dd, 1H, J1 = 8.8 Hz, J2 = 2.4 Hz); 7.25-7.21 (m, 1H); 7.20 (d, 1H, J = 8.2 Hz); 6.97-6.95 (m, 2H); 6.93 (d, 1H, J = 8 Hz) MS: 547 (M$^+$) IR: 3261, 1572, 1489, 1167 M. Pt. °C.: 133-134 |

| Example No. | Compounds and IUPAC Name | Analytical Data |
|---|---|---|
| 8 | 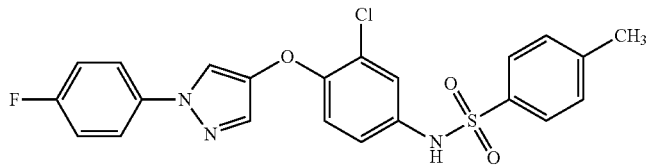<br>N-{3-Chloro-4-[1-(4-fluoro-phenyl)-1H-pyrazol-4-yloxy]-phenyl}-4-methyl-benzenesulfonamide | $^1$H NMR (CDCl$_3$): δ: 7.69 (s, 1H; 7.65 (d, 2H, J = 8.4 Hz); 7.58 (dd, 2H, J1 = 9.2 Hz, J2 = 4.8 Hz); 7.50 (s, 1H); 7.26 (d, 2H, J = 8.8 Hz); 7.16 (dd, 1H, J1 = 8 Hz, J2 = 1.8 Hz); 7.12 (d, 2H, J = 8 Hz); 6.95-6.62 (m, 2H); 6.6 (s, 1H), 2.13 (s, 3H)<br>MS: 458 (M$^+$ + 1)<br>IR: 3082, 2835, 1489, 1165<br>M. Pt. °C.: 154-155 |
| 9 | 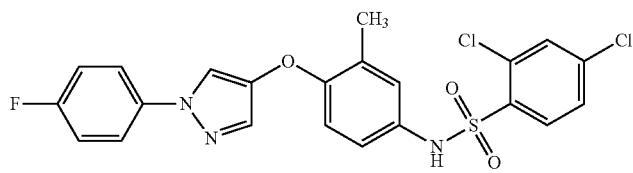<br>2,4-Dichloro-N-{4-[1-(4-fluoro-phenyl)-1H-pyrazol-4-yloxy]-3-methyl-phenyl}-benzensulfonamide | $^1$H NMR (CDCl$_3$): δ: 7.89 (d, 1H, J = 8.8 Hz); 7.60 (s, 1H); 7.58-7.53 (m, 3H); 7.45 (s, 1H); 7.31 (dd, 1H, J1 = 8.4 Hz, J2 = 2.8 Hz); 7.13 (t, 2H, J = 8 Hz); 7.05 (d, 1H, J = 6.9 Hz); 6.88-6.79 (m, 3H); 2.24 (s, 3H)<br>MS: 492 (M$^+$ + 1)<br>IR: 3157, 1573, 1514, 1166<br>M. Pt. °C.: 144-145 |
| 10 | 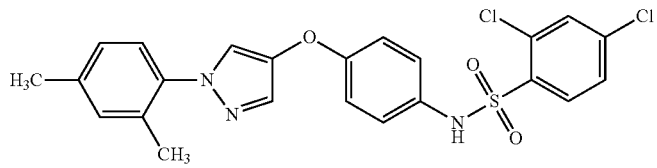<br>2,4-Dichloro-N-{4-[1-(2,4-dimethyl-phenyl)-1H-pyrazol-4-yloxy]-phenyl}-benzenesulfonamide | $^1$H NMR (CDCl$_3$): δ: 7.86 (d, 1H, J = 8.8 Hz); 7.53 (d, 1H, J = 2 Hz); 7.49 (s, 1H); 7.41 (d, 1H, J = 1.2 Hz); 7.30 (dd, 1H, J1 = 8.4 Hz, J2 = 2 Hz); 7.19 (d, 1H, J = 8.4 Hz); 7.10 (bs, 1H); 7.07 (s, 1H); 7.05 (d, 2H, J = 8.8 Hz); 6.96 (s, 1H, (—NH)); 6.92 (d, 2H, J = 8.8 Hz), 2.10 (s, 3H)<br>MS: 488 (M$^+$)<br>IR: 3089, 1500, 1168<br>M. Pt. °C.: 108 |
| 11 | 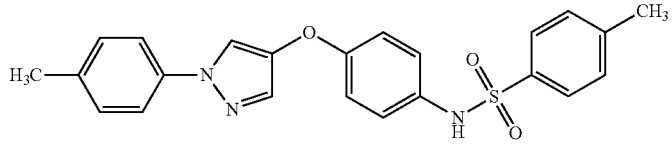<br>4-Methyl-N-[4-(1-p-tolyl-1H-pyrazol-4-yloxy)-phenyl]-benzenesulfonamide | $^1$H NMR (CDCl$_3$): δ: 7.71 (s, 1H); 7.60 (d, 2H, J = 8.4 Hz); 7.51 (d, 1H, J = 2 Hz); 7.50 (d, 2H, J = 2.48 Hz); 7.24 (d, 2H, J = 2.8 Hz); 7.22 (d, 2H, J = 2 Hz); 6.99 (d, 2H, J = 9.2 Hz); 6.94 (d, 2H, J = 9.2 Hz); 6.31 (s, 1H), 2.20 (s, 3H), 2.05 (s, 3H)<br>MS: 420 M$^+$)<br>IR: 3255, 1502, 1159<br>M. Pt. °C.: 164-165 |
| 12 | 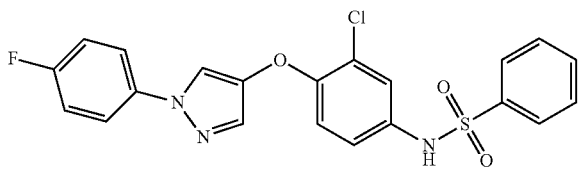<br>N-{3-Chloro-4-[1-(4-fluoro-phenyl)-1H-pyrazol-4-yloxy]-phenyl}-benzenesulfonamide | $^1$H NMR (CDCl$_3$): δ: 7.76 (d, 2H, J = 7.2 Hz); 7.70 (s, 1H); 7.60-7.56 (m, 3H); 5.49 (d, 2H, J = 9.6 Hz); 7.46 (s, 1H); 7.18-7.15 (m, 1H); 7.13 (d, 2H, J = 8.8 Hz); 6.95-6.88 (m, 2H); 6.48 (s, 1H (—NH))<br>MS: 444 (M$^+$ + 1)<br>IR: 3473, 3088, 1517, 1319, 1165<br>M. Pt. °C.: 140-141 |
| 13 | 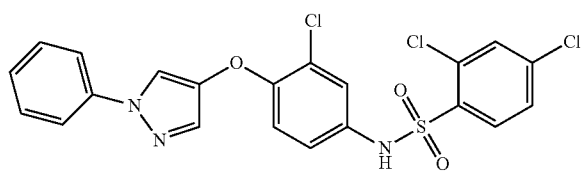<br>2,4-Dichloro-N-[3-chloro-4-(1-phenyl-1H-pyrazol-4-yloxy)-phenyl]-benzenesulfonamide | $^1$H NMR (CDCl$_3$): δ: 7.92 (d, 2H, J = 8.4 Hz); 7.75 (s, 1H); 7.62 (d, 2H, J = 7.6 Hz); 7.54 (d, 1H, J = 1.6 Hz); 7.51 (s, 1H); 7.44 (t, 2H, J = 7.6 Hz); 7.34 (dd, 1H, J1 = 8.4 Hz, J2 = 1.6 Hz); 7.29 (t, 1H, J = 7.2 Hz); 7.25 (d, 1H, J = 2.4 Hz); 7.00 (bd, 1H(NH), J = 16.4 Hz); 7.69-6.90 (m, 2H)<br>MS: 496 (M$^+$ + 2)<br>IR: 3269, 1573, 1492, 1168<br>M. Pt. °C.: 140-141 |

| Example No. | Compounds and IUPAC Name | Analytical Data |
|---|---|---|
| 14 | 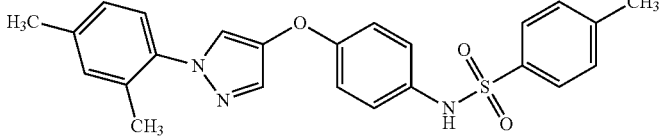<br>N-{4-[1-(2,4-Dimethyl-phenyl)-1H-pyrazol-4-yloxy]-phenyl}-4-methyl-benzenesulfonamide | $^1$H NMR (CDCl$_3$): δ: 7.60 (d, 2H, J = 8.4 Hz); 7.51 (s, 1H); 7.42 (s, 1H); 7.24-7.19 (m, 3H); 7.11 (s, 1H); 7.07 (d, 1H, J = 7.6 Hz); 6.98-6.93 (m, 4H); 6.30 (s, 1H); 2.39 (s, 3H); 2.36 (s, 3H); 2.22 (m, 3H)<br>MS: 434 (M$^+$ + 1)<br>IR: 3259, 2922, 1500, 1161<br>M. Pt. °C.: 62-64 |
| 15 | 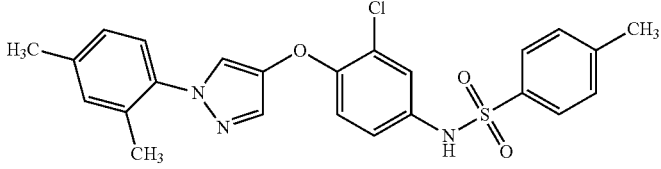<br>N-{3-Chloro-4-[1-(2,4-dimethyl-phenyl)-1H-pyrazol-4-yloxy]-phenyl}-4-methyl-benzenesulfonamide | $^1$H NMR (CDCl$_3$): δ: 7.63 (d, 2H, J = 8.4 Hz); 7.51 (s, 1H); 7.43 (s, 1H); 7.26-7.24 (m, 2H); 7.19 (d, 1H, J = 8 Hz); 7.15 (d, 1H, J = 2.4 Hz); 7.11 (s, 1H); 7.07 (d, 1H, J = 8 Hz); 6.95-6.88 (m, 2H); 6.53 (s, 1H); 2.4 (s, 3H); 2.36 (s, 3H); 2.21 (s, 3H)<br>MS: 468 (M$^+$ + 1)<br>IR: 3248, 2918, 1485, 1163<br>M. Pt. °C.: 63-65 |

EXAMPLE 16

Determination of Human PPAR Gamma Agonist Activity of Compounds of the Invention HEK-293 (Human Embryonic Kidney) cells were seeded at a density of 2.8×10$^5$ cells/well in a 6 well plate in DMEM +10% delipidated FBS medium and incubated at 37° C., 5% CO$_2$. At 70-80% confluency cells were transfected with human pCDNA3.1E~PPARγ+pGL$_2$~GAL$_4$x$_5$~Luc+pADV plasmids for 3 hours (ratio 2:0.25:1.25 μg/well). The transfection medium was then replaced with fresh medium and cells were incubated for 48 hours.

Varying final concentrations of compounds (vehicle=0.1% DMSO) of the invention were prepared in medium (50 μl/well) and added to the wells in a 96 well plate. Transfected cells were harvested and pelleted by centrifugation. The cell pellet was resuspended in medium and cells counted. 10,000 cells/well were added to the 96 well plate containing compounds of the invention and incubated for 18 hours. Luminescence produced following agonism of the PPAR gamma receptor was determined using Packard luciferase substrate reagent (100 μl/well). Light emission was quantified by counting SPC mode using a Top Count. Fold activation was calculated using the following formula:

$$\frac{CPS \text{ from [drug+ (+receptor sample)]} - CPS \text{ from [drug+ (−receptor sample)]}}{CPS \text{ from [vehicle+ (+receptor sample)]} - CPS \text{ from [vehicle+ (−receptor sample)]}}$$

| Example No. | PPARγ agonist activity |
|---|---|
| 1 | *** |
| 2 | ** |
| 3 | *** |
| 4 | *** |
| 5 | *** |
| 6 | *** |
| 7 | ** |
| 8 | ** |
| 9 | *** |
| 10 | *** |
| 11 | * |
| 12 | * |
| 13 | *** |
| 14 | * |
| 15 | ** |

All compounds show activity as PPAR gamma agonists at 30 μM. Key for relative activity:
*<8 fold increase in gene transactivation with 10 μM
**>8 fold increase in gene transactivation with 10 μM
***>8 fold increase in gene transactivation with 1 μM.

EXAMPLE 17

Anti-Inflammatory Activity of Compounds of the Invention in a Pre-Clinical Mouse Model of COPD Inflammation (Tobacco Smoke Induced Pulmonary Inflammation)

Previous studies established that the number of neutrophils recovered in the bronchoalveolar lavage (BAL) is significantly elevated 24 h following the final Tobacco Smoke (TS) exposure of 4 consecutive daily TS exposures, this time point was used in the present study.

Protocols for the exposure of mice to TS, obtaining bronchoalveolar lavage (BAL), preparation of cytospin slides for differential cell counts are as outlined below.

Exposure of Mice to TS Daily for 4 Consecutive Days

In this exposure protocol, mice were exposed in groups of 5 in individual clear polycarbonate chambers (27 cm×16 cm×12 cm). The TS from the cigarettes was allowed to enter the exposure chambers at a flow rate of 100 mL/min. In order to minimize any potential problems caused by repeated exposure to a high level of TS (6 cigarettes), the exposure of the mice to TS was increased gradually over the exposure period to a maximum of 6 cigarettes. The exposure schedule used for 4 days was as follows:

Day 1: 4 cigarettes (approximately 32 min exposure)
Day 2: 4 cigarettes (approximately 32 min exposure)
Day 3: 6 cigarettes (approximately 48 min exposure)
Day 4: 6 cigarettes (approximately 48 min exposure)

A further group of mice was exposed to air on a daily basis for an equivalent length of time as controls (no TS exposure).
Bronchoalveolar Lavage (BAL) Analysis Bronchoalveolar lavage was performed as follows: the trachea was cannulated using a Portex nylon intravenous cannula (pink luer fitting) shortened to approximately 8 mm. Phosphate buffered saline (PBS) was used as the lavage fluid. A volume of 0.4 mL was gently instilled and withdrawn 3 times using a 1 mL syringe and then placed in an Eppendorf tube and kept on ice prior to subsequent determinations.
Cell Counts:

Lavage fluid was separated from cells by centrifugation and the supernatant decanted and frozen for subsequent analysis. The cell pellet was re-suspended in a known volume of PBS and total cell numbers calculated by counting a stained (Turks stain) aliquot under a microscope using a haemocytometer.

Differential cell counts were performed as follows:
The residual cell pellet was diluted to approximately $10^5$ cells per mL. A volume of 500 μL was placed in the funnel of a cytospin slide and centrifuged for 8 min at 800 rpm. The slide was air dried and stained using 'Kwik-Diff' solutions (Shandon) as per the proprietary instructions. When dried and cover-slipped, differential cells were counted using light microscopy. Up to 400 cells were counted by unbiased operator using light microscopy. Cells were differentiated using standard morphometric techniques.
Drug Treatment Rodents such as mice and rats are obligate nasal breathers thus oral delivery of test materials (such as therapeutic agents) for inhalation will not produce good lung exposure. As a consequence, delivery of therapeutic agents to the lungs in rodents is generally achieved by intra-nasal, intra-tracheal or inhalation by whole body aerosol exposure in a chamber.

The chamber method utilises large amounts of test material and is generally reserved for inhalation toxicology studies rather than pharmacological efficacy studies. Intra-tracheal administration is a very efficient delivery method as almost all of the test material is delivered to the lungs, but this is quite an invasive technique. For studies in the mouse particularly, it is also quite technically demanding as the diameter of the trachea is quite small. The intranasal route is less invasive than the intra-tracheal route and so is particularly suitable for repeat dosing studies such as the 4 day mouse model described below. Following intranasal administration ~50% of the dose administered is delivered to the lungs (Eyles J E, Williamson E D and Alpar H O. 1999, Int J Pharm, 189(1): 75-9).

Mice were dosed intra-nasally (surrogate for oral inhalation) with vehicle (0.2% tween 80 in saline), Example 1 (0.1 mg/kg), Example 10 (0.1 mg/kg), Example 10 (0.03 mg/kg), or Example 10 (0.01 mg/kg), at 3 hours prior to tobacco smoke exposure each day. The control group of mice received vehicle 3 hrs prior to being exposed to air daily for a maximum of 50 minutes per day. BAL was performed 24 h following the final TS exposure.

In a separate experiment, mice were dosed intra-nasally (surrogate for oral inhalation) with either vehicle (0.2% tween 80 in saline), Example 7 (0.1 mg/kg), Compound 7 (0.03 mg/kg), Example 15 (0.1 mg/kg), or Example 15 (0.03 mg/kg), 1 hour prior to tobacco smoke exposure each day. The control group of mice received vehicle 1 hr prior to being exposed to air daily for a maximum of 50 minutes per day. BAL was performed 24 h following the final TS exposure.
Data Management and Statistical Analysis:

All results are presented as individual data points for each animal and the mean value was calculated for each group. Since tests for normality were positive the data was subjected to a one way analysis of variance test (ANOVA), followed by a Bonferroni correction for multiple comparisons in order to test for significance between treatment groups. A "p" value of <0.05 was considered to be statistically significant. Percentage inhibitions were automatically calculated within the Excel spreadsheets for the cell data using the formula below:

$$\% \text{ Inhibition} = 1 - \left(\frac{\text{Treatment group result} - \text{sham group result}}{\text{TS vehicle group result} - \text{sham group result}}\right) \times 100$$

Inhibition data for other parameters were calculated manually using the above formula.

As shown in Table 1, the compounds of Examples 1, 7, 10 and 15 above, when administered by a surrogate route for inhalation, significantly inhibit TS induced influx of neutrophils in the BAL.

TABLE 1

| Example No. | Inhibition of TS induced BAL neutrophil influx | p value |
|---|---|---|
| Example 1 (0.1 mg/kg) | 72% | p < 0.001 |
| Example 7 (0.1 mg/kg) | 64% | p < 0.001 |
| Example 7 (0.03 mg/kg) | 37% | p < 0.001 |
| Example 10 (0.1 mg/kg) | 72% | p < 0.001 |
| Example 10 (0.03 mg/kg) | 50% | p < 0.001 |
| Example 10 (0.01 mg/kg) | 42% | p < 0.001 |
| Example 15 (0.1 mg/kg) | 69% | p < 0.001 |
| Example 15 (0.03 mg/kg) | 66% | p < 0.001 |

EXAMPLE 18

Suitability of Compounds of the Invention for the Treatment of Lung Diseases Such as COPD when Administered by the Inhaled Route The suitability of the compounds exemplified in Examples 7, 10 and 15 above for inhalation for the treatment of lung diseases was examined by standard in vivo pharmacokinetic studies using male Wistar rats as known in the art. A single dose of 5 mg/kg of Example 7, Example 10 and Example 15 was administered in 90% Na.CMC (0.25% w/v), 10% Tween 80 (0.25%) vehicle by oral gavage and plasma samples taken at 30 minutes, 1 hour, 2 hours, 3 hours, 5 hours, 8 hours, 10 hours and 24 hours. A single 1 mg/kg dose of Example 7, Example 10 and Example 15 was administered in 10% DMSO, 10% Cremophor ELP, 10% PEG 400, 10% EtOH and 60% Milli Q Water by the intravenous (IV) route and plasma samples taken 15 minutes, 30 minutes, 1 hour, 2 hours, 3 hours, 5 hours, 8 hours, 10 hours and 24 hours. Concentrations of Example 7, Example 10 and Example 15 in the various plasma samples were determined using standard analytical procedures.

Standard pharmacokinetic parameters following IV or oral dosing were calculated from the plasma concentration data, including Area under the curve (AUC), maximum plasma concentration (Cmax), time of maximum plasma concentration (Tmax), Elimination time (Kel) and plasma half-life (T½).

Compounds suitable for inhalation for the treatment of lung diseases have low plasma AUC following i.v. dosing indicating reduced likelihood of systemic side effects. Compounds suitable for inhalation for the treatment of lung diseases also have low oral bioavailability indicated by a much lower plasma AUC following oral dosing as that achieved by i.v. dosing. Low oral bioavailability leads to only a small fraction of the swallowed drug following inhalation being absorbed into the plasma, further reducing the likelihood of systemic side effects.

TABLE 2

| Rat PK data | Example 7 | Example 10 | Example 15 | Rosiglitazone |
|---|---|---|---|---|
| Plasma AUC following 1 mg/kg i.v. dose (μg*hr/ml) | 1.08 ± 0.24 | 0.21 ± 0.06 | 0.17 ± 0.06 | 13.75*** |
| Plasma AUC following 1 mg/kg oral dose (μg*hr/ml) | 0.04 ± 0.008* | None detected** | 0.001 ± 0.002* | 14.28*** |

*Derived from 5 mg/kg oral dose PK data
**Limit of detection was 5 ng/ml
***Data from Rosiglitazone Maleate (Avandia) FDA Pharmacology review (http://www.fda.gov/cder/foi/nda/99/21071_Avandia.htm) derived from 0.4 mg/kg oral and 0.4 mg/kg i.v. dose PK dose data.

Table 2 above indicates that the compounds detailed in Example 7, Example 10 and Example 15 are particularly suitable for inhalation as they have low plasma AUC following i.v. dosing and low oral bioavailability. These properties reduce the likelihood of systemic activity (and thus systemic side effects) following inhalation. In contrast, the marketed oral PPARγ agonist Rosiglitazone which is prescribed for the treatment of diabetes has high plasma AUC following an i.v. dose and high oral bioavailability, consistent with the profile required to treat a systemic disease.

The invention claimed is:

1. A compound of formula (I) or a pharmaceutically acceptable salt thereof

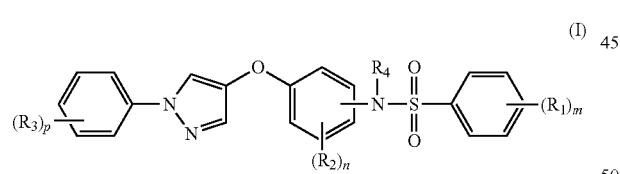

(I)

wherein,
$R_1$, $R_2$ or $R_3$ each independently represents halo, cyano, nitro, amino, alkyl, haloalkyl, alkoxy, haloalkoxy, carboxylic acid or an ester or amide thereof;
$R_4$ represents hydrogen or alkyl; and
m, n or p independently represents 0, 1, 2 or 3.

2. The compound as claimed in claim 1, wherein each $R_1$, $R_2$ and $R_3$ present in the compound is independently selected from methyl, fluoro, chloro, trifluoromethyl, methoxy, and trifluoromethoxy.

3. The compound as claimed in claim 1, wherein m, n, and p are independently 0, 1 or 2.

4. The compound as claimed in claim 1, wherein m is 0, 1 or 2.

5. A compound as claimed in claim 1 selected from the group consisting of:

2,4-Dichloro-N-[4-(1-p-tolyl-1H-pyrazol-4-yloxy)-phenyl]-benzenesulfonamide;
2,4-Dichloro-N-{3-chloro-4-[1-(4-chloro-3-trifluoromethyl-phenyl)-1H-pyrazol-4-yloxy]-phenyl}-benzenesulfonamide;
2,4-Dichloro-N-{3,5-dichloro-4-[1-(2,4-difluoro-phenyl)-1H-pyrazol-4-yloxy]-phenyl}-benzenesulfonamide;
2,4-Dichloro-N-{3,5-dichloro-4-[1-(4-fluoro-phenyl)-1H-pyrazol-4-yloxy]-phenyl}-benzenesulfonamide;
2,4-Dichloro-N-{3-chloro-4-[1-(4-fluoro-phenyl)-1H-pyrazol-4-yloxy]-phenyl}-benzenesulfonamide;
2,4-Dichloro-N-{3-chloro-4-[1-(4-chloro-phenyl)-1H-pyrazol-4-yloxy]-phenyl}-benzenesulfonamide;
2,4-Dichloro-N-{3-chloro-4-[1-(3-chloro-4-fluoro-phenyl)-1H-pyrazol-4-yloxy]-phenyl}-benzenesulfonamide;
N-{3-Chloro-4-[1-(4-fluoro-phenyl)-1H-pyrazol-4-yloxy]-phenyl}-4-methyl-benzenesulfonamide;
2,4-Dichloro-N-{4-[1-(4-fluoro-phenyl)-1H-pyrazol-4-yloxy]-3-methyl-phenyl}-benzenesulfonamide;
2,4-Dichloro-N-{4-[1-(2,4-dimethyl-phenyl)-1H-pyrazol-4-yloxy]-phenyl}-benzenesulfonamide;
4-Methyl-N-[4-(1-p-tolyl-1H-pyrazol-4-yloxy)-phenyl]-benzene
Sulfonamide;
N-{3-Chloro-4-[1-(4-fluoro-phenyl)-1H-pyrazol-4-yloxy]-phenyl}-benzenesulfonamide;
2,4-Dichloro-N-[3-chloro-4-(1-phenyl-1H-pyrazol-4-yloxy)-phenyl]-benzenesulfonamide;
N-{4-[1-(2,4-Dimethyl-phenyl)-1H-pyrazol-4-yloxy]-phenyl}-4-methyl-benzenesulfonamide; and
N-{3-Chloro-4-[1-(2,4-dimethyl-phenyl)-1H-pyrazol-4-yloxy]-phenyl}-4-methyl-benzenesulfonamide;
and pharmaceutically acceptable salts thereof.

6. A pharmaceutical composition comprising a compound as claimed in claim 1 and one or more pharmaceutically acceptable carriers or excipients.

7. The pharmaceutical composition as claimed in claim 6 which is adapted for administration by inhalation via the nose or mouth.

8. A method of treating a respiratory disease in a subject in need thereof comprising administering an effective amount of a compound as claimed claim 1 to alleviate the respiratory disease.

9. The method as claimed in claim 8 wherein the compound is administered by inhalation via the nose or mouth.

10. The method as claimed in claim 8 wherein the respiratory disease is selected from asthma, chronic obstructive pulmonary disease (COPD), allergic airway syndrome, bronchitis, cystic fibrosis and emphysema.

* * * * *